United States Patent [19]

Knorr

[11] Patent Number: 5,153,346

[45] Date of Patent: Oct. 6, 1992

[54] PROCESS FOR THE SYNTHESIS OF ALKYL METHYL-(2-CARBOALKOXY-ETHYL)-PHOSPHINATES

[75] Inventor: Harald Knorr, Frankfurt am Main, Fed. Rep. of Germany

[73] Assignee: Hoechst Aktiengesellschaft, Frankfurt am Main, Fed. Rep. of Germany

[21] Appl. No.: 637,485

[22] Filed: Jan. 4, 1991

[30] Foreign Application Priority Data

Jan. 6, 1990 [DE] Fed. Rep. of Germany ....... 4000237

[51] Int. Cl.$^5$ .............................................. C07F 9/32
[52] U.S. Cl. ....................................... 558/98; 558/179
[58] Field of Search ................................... 558/98, 179

[56] References Cited

FOREIGN PATENT DOCUMENTS 0423746 4/1991 European Pat. Off. ............ 558/179

OTHER PUBLICATIONS

Organische Phosphor Verbindungen; Sasse, K., Ed.; Georg Thieme Verlag; Stuttgart, 1963, p. 248.

March, J. Advanced Organic Chemistry; 3rd ed.; John Wiley and Sons: New York, 1985, pp. 346–347.

Chairullin, Vasjanina, Pudovik, Z. Obsc. Chim. 37 (1967), No. 3, pp. 710–714, English pp. 660–669.

Primary Examiner—Mary C. Lee
Assistant Examiner—Michael G. Ambrose
Attorney, Agent, or Firm—Curtis, Morris & Safford

[57] ABSTRACT

The compounds of the formula (I)

$$H_3C-P(=O)(OR)-CH_2CH_2COOR \qquad (I)$$

in which R is $(C_4-C_8)$alkyl are suitable as intermediates for the preparation of herbicides.

They can be prepared according to the invention, in which compounds of the formula (II)

$$CH_3P(=O)(Cl)-CH_2CH_2COCl \qquad (II)$$

are reacted with an alcohol of the formula ROH or a corresponding alcohol mixture at $-30°$ to $+50°$ C.

9 Claims, No Drawings

PROCESS FOR THE SYNTHESIS OF ALKYL METHYL-(2-CARBOALKOXY-ETHYL)PHOSPHINATES

DESCRIPTION

The present invention relates to a process for the preparation of compounds of the formula I

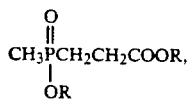

in which R in each case independently of one another is $(C_4-C_8)$alkyl, which comprises reacting a compound of the formula II

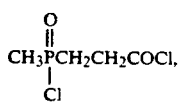

with an alcohol or a mixture of alcohols of the formula III

    (III)

in which R has the meaning given for formula I, at temperatures of $-30°$ C. to $+50°$ C.

Preferably, the R radicals in formula I have the same meaning and only one compound of the formula III is employed. The process according to the invention is particularly preferred in which R is butyl, in particular n-butyl.

The compounds of the formula I are important precursors and intermediates for the synthesis of herbicidally active substances (EP-A 30,424).

The reaction of phosphinoyl halides of simple structure with alcoholates or alcohol to give the corresponding phosphinic acid esters is known. However, the yields for this process, in particular if the use of inert solvents is dispensed with, are unsatisfactory (yield less than 50%; see Houben-Weyl, Methoden der org. Chemie (Methods of Organic Chemistry), Volume XII/1 (1983) p. 248). Product yields of about 80% can be achieved in some cases by addition of the solvent benzene.

The preparation of phosphinic acid esters of the formula I according to other literature references also leads to yields which have to be regarded as unsatisfactory for the industrial scale. Thus, only a 33 to 41% product yield is obtained, for example, according to Chairullin, Sobchuk, Pudovik, Z. obsc. Chim. 37 (1967) No. 3, pages 710-714, English pp. 660-669. Using benzene as the solvent, only 47% of theory of the desired ester is obtained with cold ethanol (Chairullin, Vasjanina, Pudovik, Z. obsc. Chim. 39 (1969) No. 2, pages 341-346).

In the presence of triethylamine as an auxiliary base, the compounds of the formula I are obtained in 50-58% yield according to Chairullin (Doklady, Akad. SSSR 162 (1965) No. 4, pages 827-828).

The alkyl phosphinates of the formula I obtained by the methods known from the literature must therefore be subjected to additional purification processes before their further processing. Moreover, the by-products which are obtained to a considerable extent have to be worked up and/or to be disposed of, which is to be judged as disadvantageous from the economical and the ecological point of view.

All of these described disadvantages are avoided in the process according to the invention, in which the desired products of the formula I can be obtained with yields of above 90% of theory. Moreover, the process according to the invention is very simple to operate and is also suitable for continuous operation.

In DE 3,934,916, it has already been proposed to prepare $(C_1-C_4)$ alkyl-methyl-(2-carbo$(C_1-C_4)$alkoxyethyl)phosphinates by reaction of a compound of the abovementioned formula (II) with $(C_1-C_4)$alcoholates in alcoholic solution.

Alcohols of the formula III which can be employed according to the invention are, for example, butanols such as n-butanol, isobutanol, and 2-butanol, pentanols such as n- and isoamyl alcohol, hexanols, heptanols and octanols.

The process according to the invention can optionally be carried out with the addition of a solvent which is inert under the process conditions. Examples of solvents of this type are optionally halogenated aromatic and aliphatic hydrocarbons.

The compound of the formula II is accessible from methyldichlorophosphane and acrylic acid (Chairullin, Sobchuk, Pudovik, Z. obsc. Chim. 37 (1967), pages 710-714).

The reaction of the compounds II and III is carried out at temperatures of $-30°$ C. to $+50°$ C., but preferably of $-10°$ C. to $+20°$ C.

The amount of alcohol of the formula III which is required is at least 2 mol per mol of compound of the formula II for reasons of the stoichiometry. The amount of alcohol is expediently increased if the compound of the formula II employed is contaminated by secondary components which can react with the alcohol of the formula III themselves, such as, for example, 1,3-dioxo-1-methyl-2-oxa-1-phospholane of the formula

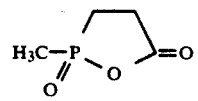

(see DE-A-2,531,238). However, the alcohol can also be used as the solvent. 2 to 4 mol of alcohol of the formula III per mol of compound of the formula II are preferably employed.

The process according to the invention can be carried out, for example, by initially introducing the alcohol of the formula III at 0° C., metering in the dichloride at this temperature and under normal pressure, subsequently stirring and then allowing to come to room temperature. The isolation of the product can be carried out by customary methods. Depending on the alcohol and additional solvent optionally used, some methods will be particularly suitable. In the case of n-butanol as the alcohol of the formula III, excess alcohol and HCl can easily be removed from the product mixture under reduced pressure and warming to 50° C. before the isolation of the product, for example, by distillation using a thin-layer evaporator.

Another possibility of the procedure is to initially introduce the alcohol of the formula III under reduced pressure and to meter in the dichloride. In this case, the pressure is preferably adjusted in the range from 1013 to 5 mbar depending on the reaction temperature in such a way that the reaction solution boils and thus a part of the hydrogen chloride is already removed during the course of the reaction. For example in the case R=n-butyl and a reaction temperature of 20° C., the pressure is about 20 mbar or 6 mbar at 0° C. After completion of the addition, the mixture is subsequently stirred, then warmed to 50° C. and residual hydrogen chloride and alcohol of the formula III are removed.

The crude material obtained is about 84-87% pure when the starting material of the formula II having a technical purity of 92% has been employed, and can be removed from the methyl-(2-carboalkoxyethyl)phosphinic acid (for example, methyl-(2-carbo-n-butoxyethyl)phosphinic acid) which is as a rule also present by distillation.

In the following examples, percentage data relate to the weight, if not stated otherwise.

EXAMPLE 1

300 ml of n-butanol (dry) are initially introduced at 0° C. and 189 g of 92% pure methyl-(2-chlorocarbonylethyl)phosphinoyl chloride (II) (0.92 mol, 92% pure by $P^{31}$-NMR) are added with stirring in the course of 1 hour. The mixture is subsequently stirred for 30 minutes and allowed to come to room temperature. Vacuum is then applied and hydrogen chloride and n-butanol are distilled off at a bath temperature of 50° C. 270.3 g of crude product which contains 84.3% of n-butyl methyl-(2-carbo-n-butoxyethyl)phosphinate (I) are obtained (93.8% of theory).

The crude product is removed from the phosphinic acid with the aid of a thin-layer evaporator at a jacket temperature of 145° C. and at 0.1 mbar. 227.3 g of product (I) which is 98.3% pure according to $P^{31}$-NMR are obtained (92.0% of theory).

EXAMPLE 2

300 ml of dry n-butanol are initially introduced at 0° C. and at 20 mbar and 189 g of technical methyl-(2-chlorocarbonylethyl)phosphinoyl chloride (II) (92% pure by $P^{31}$-NMR) are added with stirring in the course of 1 hour. The mixture is subsequently stirred at 0° C. under a reduced pressure of 20 mbar and the temperature is then allowed to come to room temperature. Residues of hydrogen chloride and n-butanol are finally removed by distillation at a bath temperature of 50° C. and under reduced pressure. 267.8 g of crude mixture which is composed to 87.2% (96.2% of theory) of n-butyl methyl-(2-carbo-n-butoxyethyl)phosphinate (I) and to 10.5% (14% of theory) of methyl-(2-carbo-n-butoxyethyl)phosphinic acid by $P^{31}$-NMR are obtained. The diester (I) is removed from the phosphinic acid by means of a thin-layer evaporator at a jacket temperature of 145° C. and at 0.1 mbar. 232.5 g of product (98.5% pure by $P^-$-NMR), which corresponds to a yield of 94.3% of theory), are thus obtained.

EXAMPLE 3

The procedure is analogous to Example 1, but the reaction temperature is 20° C. and 200 ml of n-butanol are employed instead of 300 ml of n-butanol. After removing the HCl and the excess butanol, a crude yield of 272 g containing 77% of diester (I) are obtained (87.2% of theory).

COMPARISON EXAMPLE 300 ml of absolute methanol are initially introduced at 0° C. and 189 g of technical methyl-(2-chlorocarbonylethyl)phosphinoyl chloride (II) (95.4% pure) are added in the course of 1 hour. The mixture is subsequently stirred at 0° C. for 30 minutes, allowed to come to room temperature and then concentrated in vacuo at a bath temperature of 50° C., hydrogen chloride, methyl chloride and methanol escaping 175.3 g of crude mixture which, according to $P^{31}$-NMR, contains 19.8% (20.2% of theory) of methyl methyl-(2-carbomethoxyethyl)phosphinate and 75.8% (83.9% of theory) of methyl-(2-carbomethyloxyethyl)phosphinic acid are obtained.

I claim:

1. A process for the preparation of a compound of the formula I

in which R in each case independently of one another is $(C_4-C_8)$ alkyl, which comprises reacting a compound of the formula II

with an alcohol or a mixture of alcohols of the formula III

in which R has the meaning given for formula I, at temperatures of −30° C. to +50° C.

2. The process as claimed in claim 1, wherein the reaction is carried out at temperatures from −10° C. to +20° C.

3. The process as claimed in claim 1, wherein R is butyl.

4. The process as claimed in claim 3, wherein R is n-butyl.

5. The process as claimed in claim 1, wherein hydrochloric acid and excess alcohol of the formula III formed in the reaction are removed under reduced pressure at a temperature of up to 50° C. and the crude product obtained is distilled.

6. The process as claimed in claim 1, wherein 2 to 4 mol of alcohol of the formula III are employed per mol of compound of the formula II.

7. The process as claimed in claim 1, wherein the reaction is carried out at normal pressure.

8. The process as claimed in claim 1, wherein the reaction is carried out while boiling the reaction solution in a pressure range from 1013 to 5 mbar.

9. The process as claimed in claim 2, wherein 2 to 4 mol of alcohol of formula III are employed per mol of compound of formula II.

* * * * *

UNITED STATES PATENT AND TRADEMARK OFFICE
CERTIFICATE OF CORRECTION

PATENT NO.　　:　5,153,346

DATED　　　　:　October 6, 1992

INVENTOR(S)　:　Harald KNORR

It is certified that error appears in the above-identified patent and that said Letters Patent is hereby corrected as shown below:

Column 4:

Claim 1, formula (III):  replace "ROM" with "ROH".

Signed and Sealed this

Twelfth Day of October, 1993

*Attest:*

BRUCE LEHMAN

*Attesting Officer*　　　　*Commissioner of Patents and Trademarks*